United States Patent [19]

Thoma

[11] 4,235,867
[45] Nov. 25, 1980

[54] ACRYLAMIDE COPOLYMER MATRIX FOR RADIOIMMUNE ASSAY TECHNIQUES

[75] Inventor: Hans A. Thoma, Munich, Fed. Rep. of Germany

[73] Assignee: Chandon Investment Planning Ltd., Grand Cayman, Cayman Island

[21] Appl. No.: 899,744

[22] Filed: Apr. 24, 1978

[30] Foreign Application Priority Data

May 11, 1977 [DE] Fed. Rep. of Germany ....... 2721267

[51] Int. Cl.$^2$ ...................... G01N 33/16; A61K 43/00
[52] U.S. Cl. ...................................... 424/1; 23/230 B; 424/12
[58] Field of Search ...................... 424/1, 2; 23/230 B

[56] References Cited

U.S. PATENT DOCUMENTS 4,061,466  12/1977  Sjohölm et al. .......................... 424/1

OTHER PUBLICATIONS

Goodfriend et al., Immuno Chemistry, vol. 6, May, 1969, pp. 481–484.

*Primary Examiner*—Benjamin R. Padgett
*Assistant Examiner*—Christine M. Nucker
*Attorney, Agent, or Firm*—Schwartz, Jeffrey, Schwaab, Mack, Blumenthal & Koch

[57] ABSTRACT

Disclosed is a polymer matrix based on a copolymer of acrylamide to immobilize antibodies in the radioimmunological determination of hormones and the pharmaceuticals. The specific copolymers are formed by polymerization of acrylamide and one or more copolymerizable compounds such as acrylic acid, methacrylic acid, methacrylamide, their derivatives and salts of acrylic acid or methacrylic acid.

3 Claims, No Drawings

ACRYLAMIDE COPOLYMER MATRIX FOR RADIOIMMUNE ASSAY TECHNIQUES

TECHNICAL FIELD OF THE INVENTION

The invention concerns a polymer matrix based on acrylamide to immobilize antibodies in the radioimmunological determination of hormones and pharmaceuticals.

In the radioimmunological determination of hormones and pharmaceuticals, the hormones or pharmaceuticals react with an antibody. The specificity of the reaction depends on the immunological complementariness, i.e., a cross reactivity may exist with substances exhibiting a similar chemical configuration. In an estriol-$C_6$ conjugate, the estriol is present in an immunodeterminate configuration, in which nearly all of the important functional groups of the estriol are exposed to the bonding range of the antibody. Inspite of this, estriol conjugates with the sulfate or glucuronide residue occupying the position at the phenolic $C_3$, are bonded to a considerable degree by the antibody. This is disadvantageous for the determination of free steroids, especially if the conjugate concentration exceeds the steroid concentration by orders of magnitude, as is true for the estrogens in the serum of pregnant women.

BACKGROUND OF THE PRIOR ART

For these reasons heretofore, methods were essentially used in which specificity was insured by solvent extraction prior to the radioimmune assay. Solvent extraction interferes, however, with continuous and mechanized sample processing.

In experiments to simplify radioimmunological methods by way of solid phase techniques, antibodies were bonded covalently to different matrices, such as, e.g., agar, cellulose, glass particles, polyamides and polyacrylamides; see for example U.S. Pat. No. 3,793,445 to Updike et al. The advantages of antibodies enclosed in a matrix consist of the exclusion of interfering molecules of higher molecular weight, the savings of pipetting and centrifuging steps and the extended stability of the immobilized antibodies at room temperature.

It was found that the bonding specificity of the antibody, when immobilized in the known manner in a matrix, does not satisfy desirable requirements.

SUMMARY OF THE INVENTION

It is, therefore, the object of the invention to provide a polymer matrix capable of increasing the bonding specificity of the antibody enclosed in the matrix and, thus preventing the occurrence of undesirable cross reactions.

It has been found surprisingly that a variation and increase in bonding specificity of the antibody can be obtained through the use of polymer matrices representing copolymers of acrylamide. Therefore, the subject of the invention is a polymer matrix based on a copolymer of acrylamide to immobilize antibodies in the radioimmunological determination of hormones and the pharmaceuticals. The specific copolymers are formed by polymerization of acrylamide and one or more copolymerizable compounds such as acrylic acid, methacrylic acid, methacrylamide, their derivatives and salts of acrylic acid or methacrylic acid.

The micro-environment of the polymer matrix is affected by the copolymerization of acrylamide with compounds copolymerizable with said acrylamide. The hydrophobic and hydrophylic effects and electrostatic effects within the polymer matrix are found to be dependent upon the acrylamide copolymer and provide the particularly desirable bonding specificity. By varying the polymer matrix through copolymerization, it is possible to achieve a substantial increase in the bonding specificity of the antibody and to suppress undesirable cross activities. The polymer matrix is varied through a suitable copolymerization in order to assure a specific reaction of the haptens with the immobilized antibody and to prevent the cross section reaction of haptens. Because of the increased specificity, the polymer matrices of the invention permit measurements directly in the non-extracted serum.

With the aid of the polymer matrices of the invention, highly accurate radioimmunological determinations of hormones and pharmaceuticals are possible, because the fluctuation of the values determined attributable to non-specific bonds between the steroid molecules and the matrix is minimized by the copolymerization.

In various determinations, such as, e.g., of the thyroid hormones, thyroxine and tri-iodothyronine, competitive substances are used, such as anilinonaphtholsulfonic acid, merthoilate or salicylate, in order to displace the hormones from their bond with the different bonding proteins in the serum. It is known, however, that in the case of higher concentrations of these competitive substances, the bond between the hormone and the antibody is affected. With the use of the polymer matrices of the invention, it is possible to substantially increase the concentration of the competitive substances, i.e. by a factor of 100, without weakening the hormone-antibody bond. Without fully stating the reason for this result, it is presumed that electrostatic interactions are responsible.

DESCRIPTION OF THE PREFERRED EMBODIMENTS

The acrylamide copolymer of the present invention may be prepared according to known procedures for polymerizing acrylamide monomer and other copolymerization monomers. Formation of the desired copolymer matrix arrangement is described in greater detail hereinafter.

The proportion of acrylamide in the copolymer may amount to between 1 and 99 mole %, preferably 5 to 95 mole % and, most preferably, 20 to 80 mole %. Especially suitable are copolymers of acrylamide and methacrylic acid and, more particularly, those in which the proportion of methacrylic acid amounts to 20 to 60 mole %. On the one hand, methacrylic acid yields a hydrophobic matrix and on the other hand results in a charge effect, permitting the extensive elimination of non-specific bonds of the substances to be determined.

Through the use of copolymers in accordance with the invention containing acrylic acid or methacrylic acid or salts thereof, a neutralization effect or a buffering action can be achieved for acid or alkaline solutions. This is a significant advantage in numerous determinations.

The preferred salts of acrylic acid or methacrylic acid are alkali or alkaline earth salts. Sodium and potassium salts are particularly preferred.

The preferred derivatives of acrylic acid or methacrylic acid are esters, for example, the methyl and ethyl esters.

Preferred derivatives of methacrylamide are, for example, compounds substituted at the nitrogen, such as N-hydroxymethylmethacrylamide.

An example of other compounds capable of copolymerization with acrylamide is N,N'-diallyltartardiamide.

The immobilization of the antibody takes place through inclusion in the polymer matrix and/or through covalent fixation in the polymer matrix in a known manner. A detailed description of the radioimmune assay is found, for example, in *Clinical Chemistry*, Vol. 19, No. 2, 1973, p. 145. In *Clinical Chemistry*, Vol. 19, No. 12, 1973, p. 1339 and *Clinical Chemistry*, Vol. 21, No. 7, 1975, p. 829, radioimmunological techniques are described in which immobilized antibodies are used. These descriptions are incorporated herein by reference.

The polymer matrices of the invention are suitable for the determination of different hormones and pharmaceuticals, which are present in the serum or the plasma bonded in part to specific or non-specific bonding proteins. The hormones may consist of thyroid hormones, particularly thyroxine and tri-iodothyronine, the steroid hormones, such as cortisol, testosterone, progesterone, estron, estradiol and estriol and the heart glycosides, such as digitoxin and digoxin. Vitamins, particularly, Vitamin B12 and folic acid, also pharmaceuticals with strong protein bonds, such as, for example, anti-coagulants, dicumarol, analgesics and salycilates, may further be determined.

In addition to radioimmunological determinations, alternative methods of determination, such as, fluoroimmunological determination or determination with enzymatic marking, may also be considered.

The synthesis of antigenes, the production of antisera, for example through the immunication of antibodies, are known (see for example *Clinical Chemistry*, Vol. 19, No. 2, 1973, p. 146 ff.).

The preparation of the polymer matrices of the invention with the immobilized antibodies may take place, for example, by adding a solution of the antibodies to the monomer mixture. The initial mixture is, for example, polymerized by free radical polymerization and the polymer obtained comminuted, washed and dried.

The selection and the mass proportions of the copolymers added to the acrylamide are determined by the properties of the polymer matrix desired with respect to specificity. The specificity may be influenced over a wide range of altering the hydrophobicity and the charge of the matrix. The addition of the methylacrylamide increases hydrophobicity. The addition of acrylic acid or methacrylic acid or salts thereof varies the charge of the matrix. It is possible, both to add the salts of acrylic acid or methacrylic acid directly to the monomer mixture or alternatively to polymerize the acids and subsequently form the salts in the polymer matrix through the exchange of ions.

The monomer concentration is varied to obtain a suitable pore size of the polymer matrix. A monomer concentration in the range of approximately 20% results in a pore size of approximately 7 to 10 Å.

An advantageous copolymer consists, for example, of acrylamide and 20 to 60 mole % acrylic acid and/or methacrylic acid, prepared from an approximately 20% monomer solution, where at least part of the acid groups are converted into the corresponding alkali or alkaline earth salts.

The invention will now be explained in more detail with the aid of examples.

EXAMPLE 1

In this example, the effect of the polymer matrix on the cross reactivity (K) of estriol-3-glucuronide and estriol-3-sulfate is demonstrated.

The cross reactivity K is calculated from one hundred times the amount of the mass of the corresponding hapten for y=50, divided by the required mass of the cross-reacting hapten for y=50. The values are calculated on the basis of $ID_{50}$.

The antiestriol antibody chosen displays high cross reactivity of the 3-glucuronide conjugate and the 3-sulfate conjugate.

For each polymerization mixture, the concentration was adjusted so that the total monomer concentration amounted to 2.9 mole %. For one mixture, for example, 5 g acrylamide and 1.25 g N,N'-methylbisacrylamide were dissolved in a glass beaker in 24 ml of a phosphate buffer with a pH value of 7.2. After the addition of the antibody in 1 ml phosphate buffer, the reaction was initiated with 0.15 g riboflavin and 0.10 ml N,N,N',N'-tetramethylethylenediamine and irradiated with UV light. The yellow block was subsequently comminuted, washed with distilled water and dried.

Twenty-two mg of dry antiestriol antibody gel was weighed into small columns and agitated with 0.150 ml of an incubating solution. This incubating solution contained $^3H$-estriol and unmarked hapten (estriol, estriol-3-glucuronide or extriol-3-sulfate). The temperature of the reaction was kept constant at 0° C. After an incubation period of 30 minutes, the free hapten was separated from the hapten bonded to the antibody by elution with phosphate buffer containing albumin. The eluate was collected in on a scintillation glass and diluted with 15 ml of a scintillation liquid and the radioactivity measured in a liquid scintillator. The concentration of the free indicator hapten $^3H$-estriol was calculated from the impulses.

The results of the determinations in the aqueous system and with the use of polymer matrices of acrylamide and acrylamide copolymers are summarized in the following table. The values given are the values of cross reactivity as defined in the foregoing.

|  | Aqueous System | Acrylamide | Sodium Salt Of Acrylic Acid/Acrylamid | | | Sodium Salt Of Methacrylic Acid/Acrylamid | | |
|---|---|---|---|---|---|---|---|---|
|  |  | 100 | 10:90 | 30:70 | 50:50 | 20:80 | 40:60 | 60:40 |
| Estriol-3-qlucuronide | 61 | 29 | 19 | 10 | 14 | 14 | 4 | 21 |
| Estriol-3-sulfate | 47 | 33 | 30 | 12 | 24 | 27 | 6 | 23 |

The results show that with the use of the copolymers of the invention, a significant increase in bonding specificity was obtained as compared with aqueous systems and acrylamide homopolymers outside this invention. Through the suitable selection of the copolymer, an increase in specificity by a factor of 15 can be achieved compared with aqueous systems and by a factor of 7 with respect to acrylamide homopolymers. This is demonstrated by a comparison of the values of the aqueous system and the acrylamide homopolymer with a 40/60 copolymer of methacrylic acid and acrylamide.

EXAMPLE 2

This example shows the use of the polymer matrix of the invention in a total determination of thyroxine by the enzymatic hydrolysis with pepsin.

The polymer matrix of the antibody gel consisted of a copolymer of acrylamide and 40 mole % of the sodium salt, of methacrylic acid, prepared from a 20% monomer solution.

Ten µl of serum with a thyroxine content of 18 µg per 100 ml were diluted with 160 µl of an enzyme solution, said enzyme solution consisting of 2 mg/ml pepsin dissolved in 0.1 n hydrochloric acid.

The enzyme reaction was performed at room temperature in 30 minutes.

To this, 170 µl subsequently 150 µl of a tracer solution with a content of 5.2 ng/ml of reactively marked thyroxine were added.

The entire solution was then placed on 60 mg antibody gel. The incubation period was 30 minutes, the temperature 22° C.

Evaluation resulted in an extraordinarily high recovery of 98%.

EXAMPLE 3

This example demonstrates the use of the polymer matrix of the invention in the total determination of cortisol.

The polymer matrix of the antibody gel consisted of a copolymer of acrylamide and 40 mole % of a mixture of sodium and calcium salts of methacrylic acid prepared from a 20% monomer solution.

Ten µl serum or plasma with a cortisol content of 15 µg per 100 ml were prepared. To this was added 500 µl of a tracer solution consisting of $^{125}$J-cortisol in an aqueous citrate buffer of pH 3.5.

The entire solution was then placed on 100 mg antibody gel. The incubation period was 20 minutes, the temperature 25° C.

Evaluation showed an extraordinarily high recovery of 99%.

EXAMPLE 4

This example demonstrates the use of the polymer matrix of the invention in the determination of thyroxine with the application of competitive substances.

The polymer matrix of the antibody gel consisted of a copolymer of acrylamide and 40 mole % of a mixed calcium-sodium salt of methacrylic acid prepared from a 20% monomer solution.

A tracer solution (500 µl) consisting of $^{125}$J-thyroxine in a phosphate buffer at pH 9.6 was placed on 80 mg of the antibody gel.

Further, 500 µl of the same tracer solution containing 6 mg/ml anilinonaphtolsulfonic acid, were placed on 80 mg of the antibody gel.

Both samples were incubated at a temperature of 22° C. for 20 minutes.

Evaluation showed no interference with the bond of thyroxine with the antibody in spite of the high concentration of the competitive substance present, i.e. anilinonaphtholsulfonic acid.

What is claimed is:

1. In the method of immunologically determining hormones and pharmaceuticals wherein a polymer matrix is employed for immobilizing anitbodies, the improvement comprising, the improvement comprising a polymer matrix consisting of a copolymer of acrylamide and a compound selected from the group consisting of acrylic acid, methacrylic acid, methacrylamide, their derivatives, salts of acrylic acid or methacrylic acid and mixtures thereof.

2. The improved method of claim 1, wherein the matrix is a copolymer of acrylamide and 20 to 60 mole % methacrylic acid based on acrylamide.

3. The improved method claims 1 or 2 wherein the matrix is a copolymer of acrylamide and an alkali or alkaline earth salt of acrylic acid or methacrylic acid.

* * * * *